US006716593B1

(12) United States Patent
Robins et al.

(10) Patent No.: US 6,716,593 B1
(45) Date of Patent: Apr. 6, 2004

(54) PYRIDINIUM CROSSLINKS ASSAY

(75) Inventors: Simon P. Robins, Inverurie (GB); Jeffrey D. Brady, Aberdeen (GB)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 09/479,498

(22) Filed: Jan. 7, 2000

Related U.S. Application Data

(60) Provisional application No. 60/115,098, filed on Jan. 7, 1999.

(51) Int. Cl.[7] .................. G01N 33/68; G01N 33/577

(52) U.S. Cl. .................. 435/7.92; 435/7.1; 435/7.91; 435/7.94; 435/810; 435/975; 436/512; 436/151.8; 530/387.1; 530/387.9; 530/389.1; 530/391.1

(58) Field of Search .................. 435/7.1, 7.91, 435/7.92, 7.94, 7.93, 70.21, 240.26, 240.27, 810, 975.962, 23, 967, 975, 7.13; 436/512, 518, 548, 530, 531, 86.87, 161, 808, 811, 528; 530/387.1, 387.9, 389.1, 391.1, 391.3, 323, 344, 356, 388.1, 413, 39.7, 363, 400, 404

(56) References Cited

U.S. PATENT DOCUMENTS

| | | | | |
|---|---|---|---|---|
| 5,283,197 A | * | 2/1994 | Robins | 436/87 |
| 5,472,884 A | * | 12/1995 | Eyre | 436/518 |
| 5,527,715 A | * | 6/1996 | Kung et al. | 436/547 |
| 5,620,861 A | * | 4/1997 | Cerelli et al. | 435/7.9 |
| 5,736,344 A | * | 4/1998 | Kung et al. | 435/7.9 |
| 5,756,679 A | * | 5/1998 | Daniloff et al. | 530/363 |

FOREIGN PATENT DOCUMENTS

| | | | | |
|---|---|---|---|---|
| WO | 94/14072 | | 6/1994 | G01N/33/68 |
| WO | WO 94/14072 | * | 6/1994 | G01N/33/68 |

OTHER PUBLICATIONS

Bettica, P., et al., "Comparison of the Clinical Performances of the Immunoenzymometric Assays for N–Terminal and C–Terminal Type I Collagen Telopeptides and the HPLC Assay for Pyridinium Cross–Links" *Eur J Clin Chem Clin Biochem* 35(1):63–68 (1997).

Black, D., et al., "Quantitative Analysis of the Pyridinium Crosslinks of Collagen in Urine Using Ion–Paired Reversed–Phase High–Performance Liquid Chromatography" *Anal Biochem* 169:197–203 (1988).

Bonde, M., et al., "Immunoassay for Quantifying Type I Collagen Degradation Products in Urine Evaluated" *Clin Chem* 40:2022–2025 (1994).

Eyre, D.R., et al., "Cross–Linking in Collagen and Elastin" *Ann Rev Biochem* 53: 717–748 (1984).

Eyre, D.R., et al., "Quantitation of Hydroxypyridinium Crosslinks in Collagen by High–Performance Liquid Chromatography" *Anal Biochem* 137:380–388 (1984).

Eyre, D.R., "Collagen Cross–Linking Amino Acids" *Meth Enzymol* 144:115–139 (1987).

Gomez, B., et al., "Monoclonal antibody assay for free urinary pyridinium cross–links" *Clinical Chemistry* 42(8):1168–1175 (1996).

Gunja–Smith, Z., and Boucek, R.J., "Collagen Cross–linking compounds in human urine" *Biochem. J.* 197:759–762 (1981).

Hanson, D.A., et al., "A Specific Immunoassay for Monitoring Human Bone Resorption: Quantitation of Type I Collagen Cross–linked N–Telopeptides in Urine" *J Bone Miner Res* 7(11):1251–1258 (1992).

Hanson, D.A., and Eyre, D.R., "Molecular Site Specifity of Pyridinoline and Pyrrole Cross–links in Type I Collagen of Human Bone" *J Biol Chem* 271(43):26508–26516 (1996).

James, I., and Perrett, D., "The use of capillary zone electrophoresis (CE) for the measurement of urinary pyridinoline" *Clin Rheumatol* 10(4) :457 abstract I.1 (1991).

James, I., et al., "Assay of pyridinium crosslinks in serum using narrow–bore ion–paired reversed–phase high–performance liquid chromatography" *J Chromatogr* 612:41–48 (1993).

Knott, L., and Bailey, A.J., "Collagen Cross–Links in Mineralizing Tissues: A Review of Their Chemistry, Function, and Clinical Relevance" *Bone* 22(3):181–187 (1998).

(List continued on next page.)

*Primary Examiner*—Long V. Le
*Assistant Examiner*—Lisa V. Cook
(74) *Attorney, Agent, or Firm*—Peter J. Dehlinger; Judy M. Mohr; Perkins Coie LLP

(57) ABSTRACT

Disclosed is a method for measuring a level of pyridinoline and/or deoxypyridinoline in a sample. In the method, a non-hydrolyzed sample containing one or more peptide-bound collagen pyridinium crosslinks selected from the group consisting of pyridinoline, deoxypyridinoline, or both, is contacted with a protease reagent under conditions effective for the protease reagent to cleave the crosslinks from attached collagen amino acids and peptides, so that peptide-bound forms are converted to native, peptide-free pyridinoline and deoxypyridinoline. After proteolysis, the level(s) of native, peptide-free pyridinoline and/or deoxypyridinoline are measured. Preferably, proteolysis is effective to ensure that at least 80% of total pyridinium crosslinks are present as the native, peptide-free forms. The method is particularly useful in screening or monitoring collagen degradation activity. Kits and reagents for use in the method are also disclosed.

11 Claims, No Drawings

OTHER PUBLICATIONS

Pratt, D.A., et al., "Automated Analysis of the Pyridinium Crosslinks of Collagen in Tissue and Urine Using Solid–Phase Extraction and Reversed–Phase High–Performance Liquid Chromatography" *Anal Biochem* 207:168–175 (1992).

Robins, S.P., "Turnover and cross–linking of collagen" *Collagen in Health and Disease*, Weiss and Jayson (eds), Churchill Livingstone, Edinburgh, Scotland, pp. 160–178 (1982).

Robins, S.P., et al., "Direct measurement of free hydroxy–pyridinium crosslinks of collagen in urine as new markers of bone resportion in osteoporosis" *Osteoporosis 1990*, Christiansen and Overgaard (eds), Osteopress ApS, Copenhagen, pp. 465–468 (1990).

Stivers, C.R., et al., "Development of a Urine Deoxypyridinoline Assay for the Abbott Imx System" *Clinical Chemistry* 43(6):S173 abstract #303 (1997).

* cited by examiner

PYRIDINIUM CROSSLINKS ASSAY

This application claims priority to U.S. Provisional Patent Application No. 60/115,098 filed Jan. 7, 1999, which is incorporated herein by reference.

FIELD OF THE INVENTION

The present invention relates to methods, reagents, and kits for measuring levels of total pyridinoline and/or deoxypyridinoline in fluid samples, after proteolytic digestion to remove attached amino acid residues. The invention also relates to diagnostic methods for assessing collagen degradation rates in mammals, particularly humans, and to the diagnosis and monitoring of medical conditions associated with abnormal collagen metabolism.

References

Barrett, A. J. (ed), *Meth. Enzymol.* Vol. 241, 244, and 248 (1995).

Black, D., et al, *Anal. Biochem.* 169:197–203 (1988).

Bond, J. S., and Beynon, R. J. (eds), *Proteolytic Enazymes: A Practical Approach*, IRL Press, Oxford, UK (1989).

Bonde, M., et al., *Clin. Chem.* 40:2022–2025 (1994).

Colwell, A., et al, in *Current Research in Osteoporosis and Bone Mineral Measurement, Vol. 2*, F. Ring, Editor, British Institute of Radiology, London, p. 5 (1992).

Eyre, D. R., *Ann. Rev. Biochem.* 53:717–748 (1984a).

Eyre, D. R., et al., *Anal. Biochem.* 137:380–388 (1984b).

Eyre, D. R., *Meth. Enzymol.* 144:115–139 (1987).

Gunja-Smith, Z., et al., *Biochem. J.* 197:759–762 (1981).

Hanson, D. A., *J. Bone Miner. Res.* 7:1251–1258.

Hanson, D. A., and Eyre, D. R., *J. Biol. Chem.* 271:26508–26516 (1996).

Harlow, E., et al., *Antibodies: A Laboratory Manual*, Cold Spring Harbor Lab (1988).

James, I., et al., *Clin. Rheumatol.* 10:457 (1991).

James, I., et al., *J. Chromatogr.* 612:41–48 (1993).

Knott, L., and Bailey, A. J., *Bone* 22:181–187 (1998).

Robins, S. P. in *Collagens in Health and Disease*, J. B. Weiss et al. (eds), Churchill Livingstone, Edinburgh, Scotland (1982), pp. 160–178.

Pratt, D. A., et al., *Anal. Biochem.* 207:168–175 (1992).

Robins, S. P., in *Osteoporosis1990*, Christiansen and Overgaard (eds), Osteopress ApS, Copenhagen (1990), pp. 465–467.

Segel, I., *Biochemical Calculations*, John Wiley and Sons, (1976).

BACKGROUND OF THE INVENTION

Disease conditions associated with elevated rates of collagen breakdown, especially in bone and cartilage, are responsible for considerable medical expenditures on the elderly and result in significant pain, impaired mobility, and other reductions in quality of life. Among the more common disease conditions are osteoporosis, osteoarthritis, rheumatoid arthritis, Paget's disease, metabolic bone disease, and conditions related to the progress of benign and malignant tumors in bone tissue. Other conditions associated with elevated collagen breakdown rates include osteomalacial diseases, rickets, abnormal growth in children, renal osteodystrophy, and drug-induced osteopenia. Abnormalities in bone metabolism are also often side effects of thyroid treatment and thyroid conditions per se, such as primary hypothyroidism, thyrotoxicosis and Cushing's disease.

The prevalence of collagen-related diseases of bone and cartilage has motivated a search for biochemical methods for detecting and monitoring such diseases. Various methods for diagnosing abnormalities of bone and cartilage degradation have been proposed. For example, hydroxyproline is a major constituent of the helical regions of collagens and was an early target for study as a potential marker for collagen synthesis and degradation. However, decades of study have failed to demonstrate much utility for this metabolite, in part because of substantial metabolism of hydroxyproline in the liver.

More recently, a number of assays have been proposed based on measuring certain 3-hydroxypyridinium crosslinking species known as pyridinoline (Pyd) and deoxypyridinoline (Dpd), that are excreted in urine in peptide-free and peptide bound forms. These crosslinking species are formed in collagen by condensation of the side chains derived from either three hydroxylysyl residues (for pyridinoline), or two hydroxylysyl residues and one lysyl residues (for deoxypyridinoline) (Robins, 1982, Eyre, 1984a; Eyre, 1987).

Crosslinking sites have been identified in collagen types I, II and III, and for collagen type I include lysyl/hydroxylysyl residues at positions 9N (in the N-telopeptide), 16C (in C-telopeptide), and helical residues 87, 930($\alpha$1(I)) and 933($\alpha$2(I)) (Bonde et al., 1994; Hanson and Eyre, 1996; Knott and Bailey, 1998). For example, in type I collagen, pyridinium crosslinks have been reported to occur between (i) an N-telopeptide $\alpha$1(I) site (9N position) in a first collagen fibril, (ii) an N-telopeptide $\alpha$2(I) site (9N position) from a second collagen fibril, and (iii) an internal helical site from a third collagen fibril (930H or 933H); and also between two C-telopeptide sites (16C from different chains) and another helical site (87H) (Hanson et al., 1992).

The relative abundances of Pyd and Dpd are tissue-dependent. Pyd has been found in cortical bone, trabecular bone, invertebral disc, articular cartilage, aorta, and ligament tissues. Dpd is present in trace quantities in articular cartilage and absent from invertebral disc, but is present in the other tissues just mentioned, albeit at lower frequencies than Pyd. Pyd and Dpd are absent from the collagens in normal skin, and from immature and newly synthesized collagens (Robins et al., 1990). Thus, although Pyd and Dpd are both useful in assays for measuring bone collagen degradation, Dpd appears to be more specific with respect to bone collagen (e.g., Knott et al., 1998), while Pyd may be preferred for assessing breakdown of cartilage, e.g., in rheumatoid arthritis.

For nearly 20 years, total levels of Pyd and Dpd have been measured as indicators of collagen degradation using the acid hydrolysis method of Gunja-Smith and Boucek (1981). This method utilizes an acid hydrolysis step to separate the crosslinking moieties from attached collagen polypeptide chains, followed by measurement of the hydrolysed Pyd or Dpd. Although effective to convert myriad peptide fragments to discrete peptide-free forms, the acid hydrolysis step is inconvenient, particularly for automated testing, due to the lengthy sample preparation and caustic conditions employed (e.g., 3 to 12 N HCl for up to 20 hours).

Others have investigated assays based on measuring telopeptides of collagen. For example, PCT Publications No. WO 89/04491 and WO 91/08478 (Eyre) disclose a method of detecting collagen degradation by quantitating certain 3-hydroxypyridinium-containing peptides derived from the N- and C-terminal telopeptides of type I collagen. PCT Pub. No. WO 95/08115 (Osteometer) discloses an assay for collagen fragments in a biological fluid based on the measurement of collagen-derived peptides which contain potential pyridinium crosslinking sites. PCT Pub. No. WO 94/14844 (Baylink) discloses an immunoassay method for assessing bone collagen degradation. The method employs antibodies raised against an 18 amino acid peptide consisting of residues 5 through 22 of the α1 C-telopeptide region, with the requirement that the antibodies bind to a contiguous sequence of at least six amino acids.

One difficulty with the foregoing telopeptide assays is that the measured peptides can be excreted as a spectrum of peptide variants, rather than as a single, discrete species, potentially reducing the precision of the assay. Second, it has been found that the levels of peptides can vary significantly over time in the same patient and among different patients, hindering assay reliability. Third, these methods do not distinguish Pyd from Dpd-containing fragments.

In PCT Publication WO 91/10141, it was disclosed that Pyd and Dpd are surprisingly present in peptide-free form as a substantial portion of excreted pyridinium crosslinks in biological fluids such as urine and serum, and that the levels of these native (i.e., non-hydrolysed) peptide-free forms are useful as indicators of collagen degradation rates in humans for a number of collagen disorders. Despite the absence of collagen peptides, the peptide-free crosslinks are specific for collagen degradation because the pyridinium crosslinks do not occur outside of collagen. Thus, in contrast to collagen peptide based assays, this method provides discrete metabolites that can be measured readily by various methods. Furthermore, the need for lengthy acid hydrolysis is avoided. However, the method does not measure crosslinks in the larger, peptide-bound forms, and therefore does not detect all crosslinks that are released into the blood and urine.

Accordingly, it is an object of the present invention to provide a method for measuring the level of Pyd and/or Dpd in a fluid sample that avoids the need for acid hydrolysis.

A further object is to provide a method that converts peptide-bound pyridinium crosslinks to their peptide-free forms, which simplifies detection and analysis.

A further object is to provide a method that measures total Pyd and/or Dpd crosslinks in a fluid sample using a protease reagent to cleave attached amino acid and polypeptide residues.

SUMMARY OF THE INVENTION

The present invention is based in part on the discovery by the applicants of protease compositions effective to convert peptide-bound pyridinium crosslinks to peptide-free forms, without requiring harsh conditions or time-consuming steps.

The present invention includes, in one aspect, a method for measuring a level of pyridinoline and/or deoxypyridinoline crosslinks in a sample. In the method, a fluid sample containing one or more peptide-bound collagen pyridinium crosslinks selected from the group consisting of pyridinoline, deoxypyridinoline, or both, is contacted with a protease reagent under conditions effective for the protease reagent to cleave the crosslinks from one or more attached collagen amino acids and peptides, so that peptide-bound forms are converted to native, peptide-free pyridinoline and deoxypyridinoline. After proteolysis, the levels of native, peptide-free pyridinoline and/or deoxypyridinoline are measured.

In one embodiment, the method is effective to produce a pyridinium crosslink mixture in which at least 80% of total pyridinium crosslinks are present as the native, peptide-free forms. Preferably at least 90%, and more preferably, at least 95% of the pyridinium crosslink mixture after proteolysis comprises native, peptide-free forms (N-Pyd and/or N-Dpd).

The selected native, peptide-free pyridinium crosslinks are measured by any method available in the art. In one embodiment, the crosslinks are measured by immunoassay using suitably specific antibodies. The antibodies may be monoclonal or polyclonal, or can be provided as Fc fragments or the like. In other exemplary embodiments, the crosslinks are measured chromatographically, by capillary electrophoresis, or by chemical derivatization followed by spectrophotometric or fluorescence detection. The sample is preferably a body fluid sample, and more preferably is non-hydrolysed urine or serum.

In another aspect, the invention includes a method of screening for or monitoring bone and/or cartilage collagen degradation activity in a human subject. In the method, a non-hydrolysed body fluid sample is contacted with a protease reagent under conditions effective for the protease reagent to cleave peptide-bound pyridinium crosslink species from one or more attached collagen amino acids and peptides. After proteolysis, the level of native, peptide-free pyridinium crosslinks selected from the group consisting of native, peptide-free pyridinoline and/or deoxypyridinoline, is measured, wherein a measured level that is above that characteristic of normal subjects indicates the presence of an elevated rate of bone or cartilage collagen degradation in the subject.

In another aspect, the invention includes a kit for measuring collagen pyridinium crosslinks in a sample. The kit preferably includes a protease reagent capable of cleaving pyridinoline and/or deoxypyridinoline from attached collagen amino acids and peptides, and a binding partner that is immunospecific for said pyridinoline and/or deoxypyridinoline. The kit may additionally include a predetermined amount of peptide-free pyridinium crosslinks selected from the group consisting of native, peptide-free pyridinoline (N-Pyd), deoxypyridinoline (N-Dpd), or both, for use as standards. The kit is particularly useful for practicing methods described above.

DETAILED DESCRIPTION OF THE INVENTION

I. Definitions

As used herein, the terms below have the following meanings unless indicated otherwise:

"Pyd" or "pyridinoline" or "peptide-free, non-glycosylated pyridinoline" refers to the compound shown at I below, where the pyridinium ring nitrogen derives from the ε-amino group of a hydroxylysyl residue.

"Dpd", "deoxypyridinoline" or "peptide-free deoxypyridinoline" refers to the compound shown at II below, where the pyridinium ring nitrogen derives from the ε-amino group of a lysyl residue.

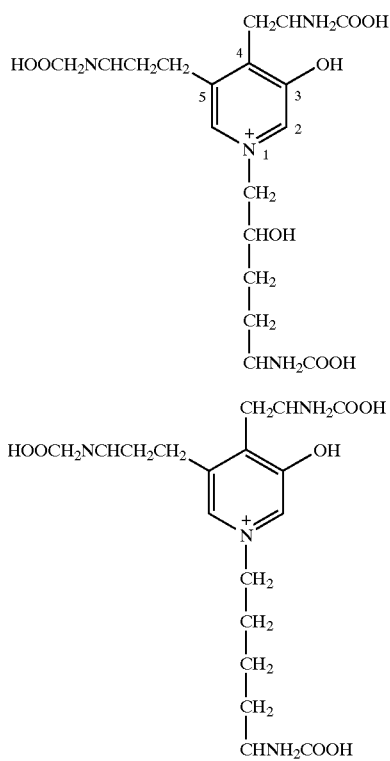

"Free crosslinks" refers to compound I, compound II, or both, i.e., pyridinoline and/or deoxypyridinoline crosslink species, free from covalently attached amino acids, peptides, and glycosyl groups.

"Glycosylated pyridinoline" or "glyco-Pyd" refers to glycosylated forms of compound I, which may be peptide-free or peptide-bound, wherein glycosyl groups are covalently bound to the aliphatic hydroxyl group. Two exemplary glyco-Pyd compounds are Gal-Pyd and Glc-Gal-Pyd.

"N-Pyd" refers to native (non-hydrolysed), non-glycosylated, peptide free Pyd. "N-Dpd" refers to native (non-hydrolysed), peptide free Dpd.

"Pyd-peptides" refers to peptide-containing forms of compound I, which may or may not contain glycosylated forms of Pyd, in which one or more of the three Pyd amino acid moieties are linked by peptide linkages to additional amino acid residues from collagen. Similarly, "Dpd-peptides" refers to peptide-bound forms of compound II, in which one or more of the three Dpd amino acid moieties are linked via peptide linkages to additional amino acid residues.

"Pyridinium-peptides" and "peptide-bound forms" refer to Pyd-peptides and/or Dpd-peptides.

"Pyd crosslinks" refers to 3-hydroxypyridinium compounds which contain compound I either in peptide-free or peptide-bound form. Pyd crosslinks include Pyd, glycosylated Pyd and Pyd-peptides. Similarly, "Dpd crosslinks" refers to pyridinium crosslinks which contain compound II in peptide-free or peptide-bound form. "Dpd crosslinks" include Dpd and Dpd-peptides.

"Pyridinium crosslinks" refers to pyridinium crosslinks which contain compounds I and/or II in peptide-free and/or peptide-bound forms.

"Total Pyd" or "T-Pyd" refers to the total quantity (or concentration) of Pyd crosslinks, i.e., peptide-free plus peptide-bound forms, with and without O-glycosylation. Similarly, "total Dpd" or "T-Dpd" refers to the total quantity of Dpd crosslinks present.

As used herein, "mammal" has its standard meaning, and includes humans, dogs, cats, horses, cows, sheep, pigs, rabbits, rats, and mice, for example.

"Body fluid" refers to any body fluid that contains compounds I and/or II in peptide-free or peptide-bound form. Exemplary body fluids include blood, serum, plasma, urine, saliva, synovial fluid, cerebrospinal fluid, and sweat, which may be subjected to one or more purification steps prior to proteolysis or analysis.

"Bone resorption abnormality" or "bone resorption condition" refers to a condition characterized by an elevated level of bone degradation (resorption) in a mammalian subject. Bone resorption conditions include osteoporosis, osteoarthritis, rheumatoid arthritis, primary hyperparathyroidism, hyperthyroidism, Paget's disease, bone cancers (e.g., metastases in bone), osteomalacia, rickets, renal osteodystrophy, and drug-induced osteopenia, for example.

II. Proteolysis Method

In one aspect, the invention includes a method of measuring the level (e.g., concentration or amount) of pyridinium crosslinks which are present in a sample. As noted above, pyridinium crosslinks from collagen occur in body fluids as heterogeneous mixtures of peptide-free and peptide-bound forms, wherein the latter may contain a variety of attached amino acid residues and polypeptide chains of varying lengths and compositions. Previous methods have been directed to measuring naturally occurring peptide-free forms or peptide-bound forms, or their sum after acid-hydrolysis of the sample. However, the significant heterogeneity of the crosslink-containing fragments has effectively prevented measurement of peptide-free and peptide-bound forms together without an acid-hydrolysis step.

For example, the antibodies described in PCT Pub. No. WO 91/08478 for binding N-telopeptides bind an epitope containing two telopeptide chains. The antibodies do not bind significantly to the separate telopeptide chains alone, and binding affinity for the dipeptide epitope is apparently not affected by photolytic ring-opening of the pyridinium ring. Apparently, the antibodies do not distinguish between Pyd and Dpd. Conversely, PCT Pub. No. WO 94/03814 (Cerelli et al.) describes antibodies that are highly specific for the native, peptide-free forms of Pyd and Dpd, but which do not cross-react significantly with peptide-bound forms having molecular weights greater than 1000 daltons.

The present invention provides an alternative method wherein peptide-bound pyridinium species are converted to corresponding native, peptide-free forms using a protease reagent that is capable of cleaving pyridinoline and deoxypyridinoline from attached collagen amino acids and polypeptide chains. Proteolysis is effective to increase the levels of native, peptide-free crosslinks (N-Pyd and N-Dpd) in the sample. (Note that the measurement of N-Pyd may optionally also include peptide-free glycosylated forms, which are typically present as about 10% of total Pyd crosslinks, although this is not essential.) The resultant peptide-free crosslinks can then be measured readily and conveniently by methods that do not require acid-hydrolysis. Preferably, the proteolysis step affords a resultant crosslink mixture that comprises at least 80%, more preferably 90% or 95%, native, peptide-free crosslinks. Most preferably, the resultant crosslink mixture comprises from 98 to 100% of the native, peptide-free forms.

The present invention can be used with any sample that is suspected of containing one or more peptide-bound collagen pyridinium crosslinks, i.e., pyridinoline, deoxypyridinoline, or both. Also, the sample should be free of substances that block the enzyme activity of the protease reagent. The sample is preferably a body fluid sample, such as urine, blood (e.g., serum or plasma), or saliva, for example. Other body fluids, such as synovial fluid, cerebrospinal fluid, and sweat are also contemplated. The sample need not be subjected to caustic chemical hydrolysis. In addition, the method may also be used with tissue and cell samples, such as from bone, cartilage, and muscle.

The protease reagent of the invention can be any protease that is capable of catalytically cleaving peptide bonds that link the α-amino and α-carbonyl groups of pyridinoline and deoxypyridinoline to amino acids and peptides derived from collagen. Numerous proteases have been characterized in the art with respect to substrate specificities, kinetic parameters, pH optima, cofactor requirements, and the like, and are commercially available or can be isolated by known methods. With regard to substrate specificity, the protease reagent is preferably selective for cleaving residues immediately adjacent to the α-carbons which link the 3-hydroxypyridinium crosslinks to the source collagen chains, by virtue of recognizing at least a portion of the 3-hydroxypyridinium moiety. Alternatively, the protease reagent can be nonspecific with respect to substrate amino acid sidechains, provided that it cleaves the pyridinium crosslinks from attached collagen amino acid residues. Exemplary non-specific or low specificity proteases include bromelain, papain, subtilisin, pepsin, proteinase K, human cathepsin S, and thermolysin. Proteolysis conditions and commercial sources for such enzymes are well known (e.g., Barrett, 1995; Bond, 1989; Worthington Enzyme Catalog 1997–98, Sigma Catalog, 1998). It is also contemplated that the protease reagent may contain two or more proteases which together provide the required cleavage properties.

The protease reagent may be obtained from any suitable source, usually from a biological or commercial source. Preferred mammalian tissue sources include kidney and liver tissues which preferably are prepared from an organ such as kidney or liver from pig, sheep, cow, dog, guinea pig, rat, mouse, or human. The source tissue is preferably homogenized carefully using a standard homogenizer device, followed by optional passage through cheese cloth or like material to remove large size debris. The homogenized material may be pelleted by centrifugation to remove cells and other particulate matter, yielding a protease-containing supernatant. The supernatant may be frozen for storage and also to precipitate additional components from the mixture. The supernatant can be dialyzed to remove small molecules such as endogenous peptide-free Pyd and Dpd.

The protease reagent can also be obtained from appropriate cell cultures, such as mammalian renal and hepatic cell lines which are readily available from the American Type Culture Collection (ATCC) located at 10801 University Blvd., Manassas, Va. 20110–2209. If necessary, the cells are lysed by standard methods, e.g., sonication or exposure to detergent, to release the proteases from the cells. The protease reagent may be used as an extract or may be further purified if desired. In addition, the reagent may further include one or more glycosidases to convert any glycosylated forms of Pyd to the aglycone form.

In practicing the proteolysis method of the invention, the sample in which the Pyd and/or Dpd crosslinks are to be measured is reacted with the protease reagent under conditions effective for the protease reagent to cleave such crosslinks from one or more attached collagen amino acids and peptides. The protease reagent may be added as a stock solution or as a dried reagent. For example, a urine or serum sample is reacted with an appropriate amount of protease reagent sufficient to achieve the desired level of proteolysis of pyridinium-containing peptides, e.g., by mixing the sample with an approximately equal volume of protease reagent solution. The pH of the reaction mixture is preferably adjusted to promote proteolysis at a pH optimum of the protease reagent. This may be accomplished by including an appropriate buffer, such as a phosphate/citrate buffer, which may be titrated further by adding an appropriate amount of acid or base. The pH optimum can be readily determined by measuring the extent of proteolysis of pyridinium peptides under a range of different pH conditions, as illustrated in Example 2. Thus, for the kidney protease preparation described in Example 1, the pH of the buffer is preferably between 2 and 9, more preferably between 4 and 7, and more preferably still is about 5.

The sample proteolysis conditions may additionally include one or more cofactors that promote the activity of the protease reagent. Such cofactors include metal ions such as zinc ion, for metalloproteinases, thiols such as 2-mercaptoethanol and dithiothreitol, for cysteine proteases, and ATP for ATP-dependent proteases. One or more protease inhibitors may also be included during initial stages of purification to inhibit endogenous proteases other than those of interest. Such protease inhibitors are well known and are commercially available individually or as mixtures (e.g., Worthington Catalog or Sigma Catalog, supra).

Since Pyd and Dpd crosslinks are light-sensitive, crosslink-containing samples and reaction mixtures are preferably protected from light until measurement is complete, e.g., using amber-colored containers and low light conditions, to minimize photo-degradation of the pyridinium moieties.

Proteolysis is complete when the desired amount of cleavage has occurred. The duration of proteolysis can be selected according to prior experiments to determine the rate of cleavage for the selected sample type and proteolytic conditions, by incubating the sample with protease reagent and withdrawing aliquots periodically to measure the levels of peptide-free pyridinium crosslinks as a function of time. Preferably, proteolysis is allowed to occur for between 30 minutes and 24 hours, depending on the level of protease activity used and the degree of cleavage desired, although longer and shorter time periods are also contemplated. Also, it may also be advantageous to add the protease reagent to the sample in two or more aliquots at selected time intervals. For example, after reaction with a first protease aliquot for one to eight hours, a second aliquot can be added for incubation for an additional period of time.

After proteolysis, the level(s) of the selected native, peptide-free pyridinium crosslinks are measured by any suitable technique, such as immunoassay, chromatography, or capillary electrophoresis.

For example, N-Pyd and N-Dpd may be measured by immunoassay techniques employing antibodies specific for N-Pyd, N-Dpd, or both. The antibodies may be monoclonal or polyclonal, as described further below. With regard to specificity, the antibodies should be sufficiently specific for the selected crosslinks (N-Pyd and/or N-Dpd) to avoid spurious results due to binding other components in the sample.

Screening and selection for such antibodies may be based on affinity for N-Pyd or N-Dpd alone, where an antibody showing an affinity for N-Pyd and/or N-Dpd of greater than about $10^7$/molar, preferably greater than about $10^8$/molar, is usually specific enough for the purposes of the invention. Binding affinity can be determined by known methods, e.g., by Scatchard analysis using an ELISA assay (Campbell, 1991; Segel, 1976). Accordingly, in one embodiment, the antibody has a binding affinity constant for the selected free crosslink species of greater than about $1 \times 10^7$/molar, and preferably greater than about $1 \times 10^8$/molar.

In addition, the screening process for antibodies may be based on additional binding criteria, such as low affinities for amino acids, polypeptides, and/or other possible sample components. For this purpose, it is convenient to measure the binding affinities of the antibodies with respect to certain pyridinium peptide forms that are obtainable from urine, such as pyridinium peptides having molecular weights greater than about 1000 MW prepared by dialysis as described in Example 2 of PCT Pub. No. WO 94/03814. A high affinity for the selected free crosslinks (N-Pyd and/or N-Dpd) in combination with a relatively low affinity for N-Pyd or N-Dpd peptide forms (e.g., a binding affinity ratio of less than about 3:1, preferably less than about 5:1, for free:peptide forms) is thus one additional criterion that can be used in the screening process. Accordingly, in one general embodiment, the antibodies have a ratio of reactivity toward the selected native free pyridinium crosslink and urinary pyridinium peptides larger than 1,000 daltons in molecular weight, of greater than about 3:1, more preferably greater than about 5:1.

As another binding criterion, the antibodies can be tested for cross-reactivity with free amino acids. For this purpose, an amino acid mixture comprising all 20 standard amino acids at selected concentrations can be used, such as the amino acid mixture employed in Example 10 of WO 94/03814.

The antibodies for use in the invention may be specific for N-Pyd, N-Dpd, or both, including antibodies which are specific for one and have moderate crossreactivity (e.g., 40%) with the other. In a more specific embodiment, where the antibody is highly specific for N-Pyd, the antibody preferably has a ratio of reactivity toward native free pyridinoline and native free deoxypyridinoline of greater than about 5:1, preferably greater than about 20:1, and more preferably greater than about 100:1. Where the antibody is for binding N-Dpd, the antibody preferably has a ratio of reactivity toward native free deoxypyridinoline and native free pyridinoline of greater than about 5:1, preferably greater than about 25:1, and more preferably greater than about 100:1. Where the antibody is for binding both native free pyridinoline and native free deoxypyridinoline, the antibody preferably has a ratio of reactivity toward native free pyridinoline and native free deoxypyridinoline of between about 2:1 and 1:2. Antibodies having such properties, and methods for preparing them, are disclosed in PCT Pub. Nos. WO 96/27134 (Kung et al.), WO 96/07906 (Winterbottom et al.), WO 94/14072 (Kung et al.), WO 94/03814 (Cerelli et al.), and WO 91/10141 (Robins), all of which are incorporated herein by reference.

Reaction of sample with specific antibodies can be carried out by any of a variety of immunoassay configurations known in the art, including homogeneous and heterogeneous assay formats. Any appropriate technique for detection can be used, such as radioimmunoassay, coupled enzymes, UV-VIS absorbance, fluorescence, chemiluminescence, or an EMIT configuration. One preferred reporter is alkaline phosphatase, which can react with a p-nitrophenylphosphate substrate to produce a colored product having a strong absorption peak at 405 nm. It will be appreciated that various other detection modes may be employed, such as a biotin-labeled second antibody in combination with a reporter-labeled streptavidin.

In an exemplary embodiment of the assay method, a known volume, typically 10–50 µL, of sample is added to an immunogen-coated solid support, e.g., the wells in a microtitre plate, and sample addition is followed by addition of a known volume, typically 50–200 µL, of immunogen-specific antibody of a known dilution. The mixture on the solid support surface is then incubated, preferably under conditions effective to achieve equilibrium between the antibody binding to sample crosslinks and surface-bound immunogen (e.g., overnight at 2–8° C. or at room temperature for several hours).

After the incubation, the solid support is washed several times to remove antibody not specifically bound to the support, and is then incubated with an enzyme-labeled anti-IgG antibody effective to bind specifically to support-bound antibody. For example, where the immunogen-specific antibody is a rabbit polyclonal antibody, the enzyme-labeled antibody can be goat anti-rabbit IgG conjugated with alkaline phosphatase. For a mouse monoclonal antibody reagent, the enzyme-labeled antibody can be a goat anti-mouse IgG derivatized with alkaline phosphatase.

After a short incubation time, the support is again washed to remove non- specifically bound material, and the level of enzyme bound to the support is determined by addition of enzyme substrate, with spectrophotometric determination of converted substrate.

For calibration of the assay, standards containing a range of immunogen concentrations are added in duplicate to some of the wells, to generate a standard curve. Up to 40 samples are then added in duplicate to remaining wells, and the wells are then assayed as above.

Preferably, the immunoassay utilizes a competitive, heterogeneous immunoassay format in which the reporter label for detection of the immunocomplex is directly attached to either a competitor immunogen or to the immunogen-specific antibody.

Thus, in one preferred configuration, the immunogen-specific antibodies are immobilized on a solid support, and enzyme-labeled immunogen is added to compete with peptide-free crosslinks in the sample, for binding to the immobilized antibodies. The enzyme label can be alkaline phosphatase or horse-radish peroxidase, for example. In a second preferred configuration, immunogen is immobilized on a solid support to compete with peptide-free crosslinks in the sample for binding to non-immobilized enzyme-labeled antibody. In addition, the crosslinks can be measured using an automated immunoassay cassette, as described in PCT Pub. No. WO 98/37416 (Jones).

In other embodiments, the crosslinks can be measured by fluorescence detection based on their intrinsic fluorescence properties. N-Pyd and N-Dpd strongly fluoresce with peak emission at 390–400 nm when subjected to an excitation source at about 297 nm. Chromatographic (Black et al., 1988; Eyre et al., 1984b, James et al., 1993) and capillary electrophoresis techniques (James et al., 1991) for fluorimetrically measuring Pyd and Dpd have been described. The crosslinks may also be measured based on UV-absorbance properties as described by Colwell et al. (1992).

Where the sample fluid tested is urine, the level of measured crosslinks may be normalized using a measured level of creatinine or any equivalent thereof, by conventional methods. Blood samples may be converted to serum or plasma by known methods, and may be subjected to further pre-processing if desired. For example, serum can be passed through a spin-filter having a defined molecular weight cutoff to remove proteins of a selected size from the sample prior to assay.

The proteolysis method of the invention can be adapted to a method of screening for or monitoring bone and/or cartilage collagen degradation activity in a human subject. In the method, a non-hydrolysed body fluid sample is contacted with a protease reagent as described above under conditions effective for the protease reagent to cleave peptide-bound pyridinium crosslink species from one or more attached collagen amino acids and peptides. After proteolysis, the level of native, peptide-free pyridinium crosslinks selected from the group consisting of native, peptide-free pyridinoline and/or deoxypyridinoline, is measured, wherein a measured level that is above that characteristic of normal subjects indicates the presence of an elevated rate of bone or cartilage collagen degradation in the subject.

In practicing this aspect of the invention, it is usually necessary to ascertain an average level or range of the selected free crosslinks which is characteristic of normal subjects for the particular mode of sample collection selected, to provide a standard against which levels measured in test subjects may be compared. Thus, free crosslink levels will ordinarily be measured in samples from control subjects who are in good health. The makeup of the control group may be tailored according to the characteristics of the population to be tested. For example, the control group may be limited to a particular age group, e.g. 25–55 year old males, or 25–44 year old premenopausal females, to obtain baseline levels. Other parameters of interest may include the subjects weight, race, or gender for example. The determined average or range of free crosslinks in the normal subjects is then used as a benchmark for detecting above-normal levels indicative of an abnormally elevated rate of collagen degradation. In a related embodiment, the invention can also be applied as a prognostic indicator for likelihood of bone fracture, such that the likelihood of fracture increases in proportion to the degree of elevation of the measured crosslink level.

III. Crosslink Proteolysis Kit

The invention also includes a kit for measuring collagen pyridinium crosslinks in a sample. The kit preferably includes a protease reagent as described above, which is capable of cleaving pyridinoline and/or deoxypyridinoline from attached collagen amino acids and peptides, and a binding partner, such as an antibody or any equivalent thereof, that is immunospecific for said pyridinoline and/or deoxypyridinoline. The kit may additionally include a pre-determined amount of peptide-free pyridinium crosslinks selected from the group consisting of native, peptide-free pyridinoline, deoxypyridinoline, or both, for generating a standard curve. Thus, for immunoassay formats, the kit may include an antibody of the type described above, and any other suitable reagents for carrying out the assay. The assay format may be heterogeneous or homogeneous, and can have a competitive or non-competitive format such as discussed above. The kit may further include instructions for conducting the steps of an assay method for the selected crosslinks.

IV. Utility

The method of the invention is especially useful for converting heterogeneous pyridinium crosslink mixtures to a more homogeneous form (i.e., peptide-free) in which pyridinium crosslinks are easier to quantify. When a substantial proportion (greater than about 80%) of the crosslinks is provided in the native, peptide-free form, the method provides a useful measure of the total level of the selected pyridinium crosslinks in the sample.

The invention thus also provides a method of screening for or monitoring bone and/or cartilage collagen degradation activity in a human subject. The method may be used in a screening embodiment or to detect (diagnose) non-invasively the presence of a bone or cartilage disorder characterized by above-normal collagen degradation. Exemplary disorders for which the invention may be used include osteoporosis, osteoarthritis, rheumatoid arthritis, and conditions related to the progress of benign and malignant tumors of bone, and metastatic cancers that have migrated to bone cells from elsewhere in the body, e.g., from prostate or breast initial tumors. Other conditions of interest include osteomalacial diseases, rickets, abnormal growth in children, renal osteodystrophy, and drug-induced osteopenia.

The method may also be used to monitor the progress of an ongoing bone collagen disorder over time, or to monitor a subject's response to therapeutic treatment. A number of anti-resorptive therapies are now under development or are already available for which the invention will be useful, such as alendronate and pamidronate-based therapeutic regimens. Similarly, the method may be used in the context of metastatic cancer conditions, to determine whether a primary cancer has spread to the subject's bone tissue, and whether a subject is responding to treatment.

It will be appreciated that the method may also be used with other diagnostic methods, such as radiographic techniques, ultrasound, and assays directed to other indicators of bone resorption and/or formation status, to provide a fuller picture of the subject's status.

From the foregoing, it will be appreciated how various objects and features of the invention are met. The invention provides a simple method for converting peptide-bound pyridinium crosslinks in a sample to peptide-free forms without requiring caustic acid hydrolysis. The complexity of pyridinium crosslinks in the sample is reduced by transforming many peptide-bound forms to the discrete, peptide-free species, N-Pyd and N-Dpd, which can be conveniently measured by known methods. The invention thus provides a simple way of measuring total pyridinium crosslinks in a sample.

The invention may be further understood in light of the following examples, which are not intended to limit the scope of the invention.

EXAMPLE 1

Isolation of Protease Activity

Pig kidneys were obtained from a local abattoir. After dissection, cortex tissue (240 g wet weight) was homogenised in a buffer of 0.5 mM Tris-HCl, pH 7.4, containing 0.25 M sucrose (final volume 300 mL). Undisrupted cells and connective tissue were pelleted by centrifugation at 1000×g for 2 min. The supernatant was frozen at −80° C. The supernatant was thawed and dialysed against two changes of phosphate buffered saline (PBS, containing 10 mM sodium phosphate, 140 mM NaCl, pH 7.4, 1liter per dialysis) to remove endogenous Pyd and Dpd. HPLC analysis indicated that the two dialysis steps were effective to reduce the concentration of endogenous N-Pyd in the homogenate supernatant from 3.5 $\mu$M to 0.11 $\mu$M, and N-Dpd from 0.6 $\mu$M to 0.02 $\mu$M, respectively.

EXAMPLE 2

Characterization of Protease Activity

Dialysed supernatant from Example 1 (100 μL) was incubated with human urine samples (100 μL, non-hydrolysed) and 400 μL of buffer having a pH of 5, 6, or 7; prepared by titrating 100 mM sodium citrate with an appropriate volume of 100 mM disodium hydrogen phosphate. Boiled homogenate was used as a negative control. The incubation mixtures were incubated at 37° C. overnight, after which the sample was acidified to pH 2 with HCl. Any sediment was removed by centrifugation. The supernatant was passed through CF1 cellulose powder (Whatman Biosystems Ltd., UK) using an ASPEC system as described in Pratt et al. (1992).

The purified samples were analysed by HPLC to measure the levels of N-Pyd and N-Dpd. The results showed that for each buffer, proteolytic cleavage occurred, leading to increased levels of N-Pyd and N-Dpd. Further, proteolytic activity increased in proportion to buffer acidity, with the greatest level of activity being observed at pH 5. Incubation at pH 5 afforded N-Dpd at a level that was 93% of total Dpd in the sample, and N-Pyd at a level that was approximately 75% of total Dpd.

Although the invention has been described with respect to particular embodiments, it will be appreciated that various modifications can be made without departing from the invention.

What is claimed:

1. A method for measuring a level of pyridinoline and/or deoxypyridinoline crosslinks in a fluid sample, said method comprising
   providing a fluid sample that contains one or more peptide-bound collagen pyridinium crosslinks selected from the group consisting of pyridinoline, deoxypyridinoline, or both,
   contacting the sample with a protease reagent under conditions effective for the protease reagent to cleave said crosslinks from one or more attached collagen amino acids and peptides, to form native, peptide-free pyridinium crosslinks and
   after said contacting, measuring a level of said native, peptide-free pyridinium crosslinks selected from the group consisting of native, peptide-free pyridinoline and/or native, peptide-free deoxypyriinoline, in the sample.

2. The method of claim 1, wherein the measured level is at least 80% of the total level of the selected collagen pyridinium crosslinks in the sample.

3. The method of claim 1, wherein the measured level is at least 90% of the total level of the selected collagen pyridinium crosslinks in the sample.

4. The method of claim 1, wherein said selected crosslinks are native, peptide-free deoxypyridinoline.

5. The method of claim 1, wherein said selected crosslinks are native, peptide-free pyridinoline.

6. The method of claim 1, wherein said selected native, peptide-free crosslinks are measured by immunoassay using antibodies specific for the selected native, peptide-free crosslinks.

7. The method of claim 6, wherein said antibodies are monoclonal antibodies.

8. The method of claim 6, wherein said antibodies are polyclonal antibodies.

9. The method of claim 1, wherein said selected native, peptide-free crosslinks are measured chromatographically.

10. The method of claim 1, wherein said sample is a non-hydrolysed urine sample.

11. The method of claim 1, wherein said sample is a non-hydrolysed blood sample.

* * * * *